(12) United States Patent
Godavarty et al.

(10) Patent No.: US 9,709,733 B2
(45) Date of Patent: Jul. 18, 2017

(54) HAND-HELD OPTICAL PROBE BASED IMAGING SYSTEM WITH 3D TRACKING FACILITIES

(75) Inventors: Anuradha Godavarty, Miami, FL (US); Steven A. Regalado, Miami, FL (US); Bhavani Jayachandran, Miami, FL (US); Banghe Zhu, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 2517 days.

(21) Appl. No.: 12/442,505

(22) PCT Filed: Sep. 28, 2007

(86) PCT No.: PCT/US2007/079906
§ 371 (c)(1),
(2), (4) Date: Jun. 26, 2009

(87) PCT Pub. No.: WO2008/039988
PCT Pub. Date: Apr. 3, 2008

(65) Prior Publication Data
US 2010/0010340 A1     Jan. 14, 2010

Related U.S. Application Data

(60) Provisional application No. 60/847,812, filed on Sep. 28, 2006.

(51) Int. Cl.
*A61B 5/05* (2006.01)
*G02B 6/06* (2006.01)
(Continued)

(52) U.S. Cl.
CPC .............. *G02B 6/06* (2013.01); *A61B 5/0091* (2013.01); *A61B 5/064* (2013.01); *A61B 5/4312* (2013.01);
(Continued)

(58) Field of Classification Search
USPC ........ 600/407, 424, 425, 427, 437, 473, 476
See application file for complete search history.

(56) References Cited

U.S. PATENT DOCUMENTS 5,730,133 A     3/1998  Godik
5,830,145 A *  11/1998  Tenhoff ......................... 600/463
(Continued)

FOREIGN PATENT DOCUMENTS

DE    10 2005 058 598    7/2006

OTHER PUBLICATIONS

Culver, J.P. et al., "Three-dimensional diffuse optical tomography in the parallel plane transmission gemoetry: Evaluation of a hybrid frequency domain/continuous wave clinical system for breast imaging", Medical Physics, vol. 30, No. 2, pp. 235-347, 2003.
(Continued)

*Primary Examiner* — Tse Chen
*Assistant Examiner* — Jason Ip
(74) *Attorney, Agent, or Firm* — Marshall, Gerstein & Borun LLP

(57) ABSTRACT

The claimed method and system uses a hand-held based optical process to image large tissue volumes using a flexible probe head, increased data acquisition using multi-source illumination and multi-detector sensing, and tomographic reconstruction of sub-surface structures of a target object using ultrasonic tracking facilities.

22 Claims, 19 Drawing Sheets

(51) Int. Cl.
  *A61B 5/00* (2006.01)
  *A61B 5/06* (2006.01)
  *G01N 21/359* (2014.01)
  *G01N 21/47* (2006.01)
  *G02B 6/08* (2006.01)
  G01N 21/64 (2006.01)
  G01N 21/17 (2006.01)

(52) U.S. Cl.
  CPC ......... *G01N 21/359* (2013.01); *G01N 21/474* (2013.01); *G01N 21/4795* (2013.01); *G02B 6/08* (2013.01); G01N 21/6456 (2013.01); G01N 2021/1787 (2013.01); G01N 2021/4742 (2013.01); G01N 2201/0221 (2013.01); G01N 2201/0826 (2013.01); G01N 2201/0833 (2013.01)

(56) References Cited

U.S. PATENT DOCUMENTS

| | | | |
|---|---|---|---|
| 6,795,195 B1 | 9/2004 | Barbour et al. | |
| RE38,800 E * | 9/2005 | Barbour | 600/407 |
| 8,070,682 B2 * | 12/2011 | Zhu | 600/437 |
| 2002/0045811 A1 | 4/2002 | Kittrell et al. | |
| 2004/0215072 A1* | 10/2004 | Zhu | 600/407 |
| 2004/0254464 A1* | 12/2004 | Stribling | 600/437 |
| 2005/0116179 A1* | 6/2005 | Aguirre et al. | 250/492.1 |
| 2007/0219450 A1 | 9/2007 | Azar et al. | |

OTHER PUBLICATIONS

Ge, J., et al., "A novel optical imager towards breast cancer diagnosis," Medical Physics, vol. 33, No. 6, p. 1989, 2006.

Godavarty, A. et al., "Fluorescence-enhanced optical imaging of large phantoms using single and simultaneous dual point illumination geometries," Medical Physics, vol. 31, No. 2, pp. 183-190, 2004.

Jayachandran, B. et al., "Design and development of a hand-held optical probe toward fluorescence diagnostic imaging", Journal of Biomedical Optics, vol. 12, No. 5, pp. 054014-1-10, 2007.

International Search Report for PCT/US2007/079906, mailed Feb. 23, 2009.

* cited by examiner

| Imaging Modality | Principle | Advantages | Disadvantages |
|---|---|---|---|
| X-ray | Uses x-rays of ~ 50 KeV photons to detect the x-rays attenuated by tissues of differing densities | Excellent resolution<br>Good penetration depth | Ionizing radiation<br>Poor contrast among soft tissues<br>Overlooks 10% of breast cancer in non-calcified lesions |
| Computer Tomography (CT) | Uses x-rays at different angles for cross-sectional views | Same as x-ray technique, but provides more information | Greater exposure to x-ray radiation |
| Ultrasound (US) | Uses high frequency sound waves to detect the reflectance and transmittance from acoustically dissimilar tissues | Non-ionizing radiation<br>Inexpensive<br>Portable, safe, and versatile | Poor imaging quality<br>Poor contrast |
| Magnetic resonance imaging (MRI) | Uses strong magnetic fields and RF waves to detect the emitted RF waves and relaxation of spin state of nuclei in tissues | Non-ionizing radiation<br>Functional imaging<br>Soft-tissue contrast<br>Good resolution<br>Good penetration depth | Strong magnetic field<br>Expensive<br>Not portable<br>Slow process |

Figure 1

Circular

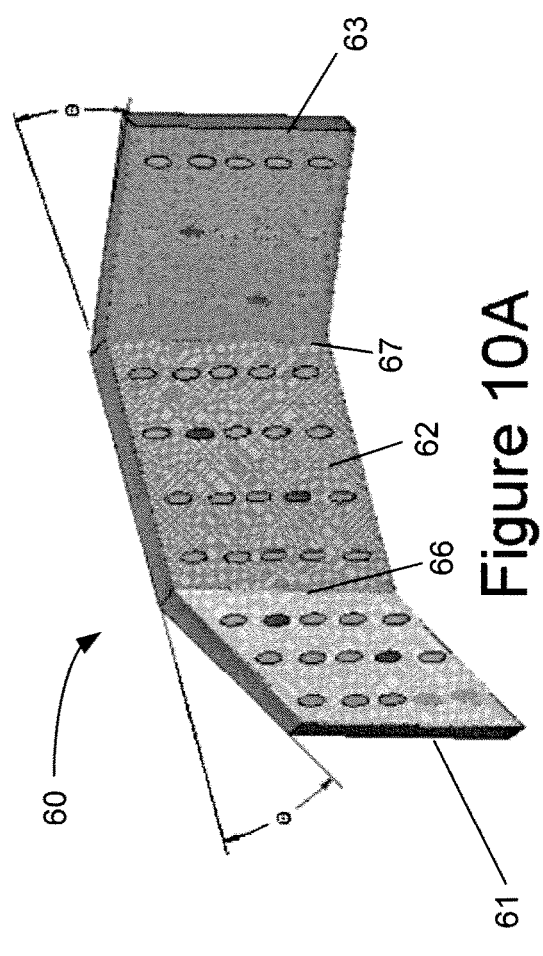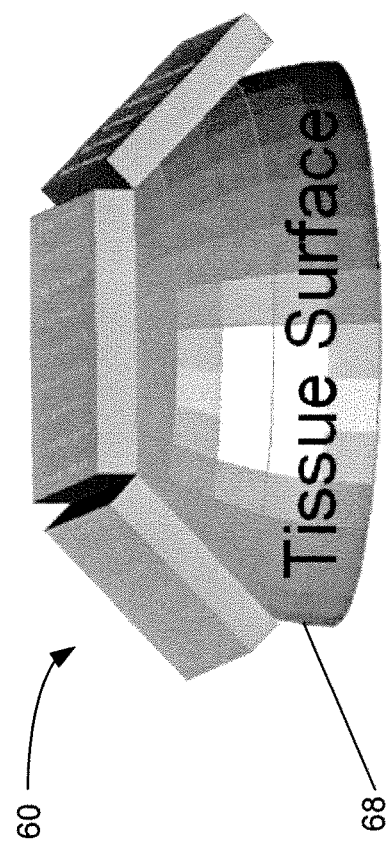
Figure 10A
Figure 10B

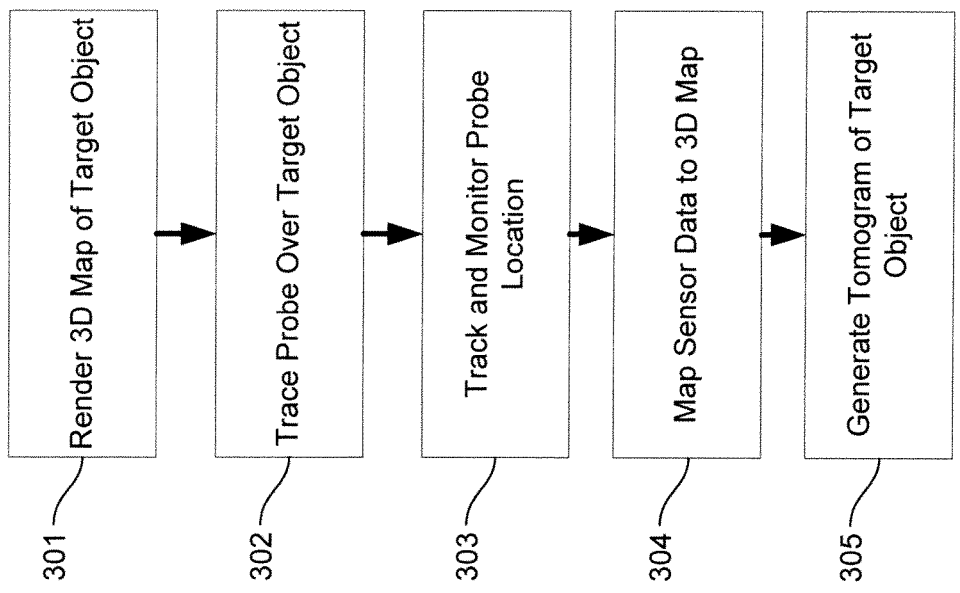

HAND-HELD OPTICAL PROBE BASED IMAGING SYSTEM WITH 3D TRACKING FACILITIES

This application claims the benefit of U.S. Provisional Patent Application Ser. No. 60/847,812, filed Sep. 28, 2006, the entirety of which is hereby incorporated by reference herein.

BACKGROUND

Existing diagnostic imaging techniques of breast cancer include X-ray mammography, computer tomography (CT), ultrasound, magnetic resonance imaging (MRI), and nuclear imaging. FIG. 1 illustrates a table summarizing the advantages and disadvantages of each existing diagnostic imaging process or technique. These conventional techniques may be limited by poor resolution, use of harmful ionizing radiation, lack of portability, and/or expensive instrumentation.

Near-infrared (NIR) optical imaging is an emerging non-invasive technology that may be applied towards deep tissue imaging, with one application being breast cancer diagnostics However, the existing NIR optical imaging systems may be limited in a number of ways. For example, existing NIR imaging apparatus may be large and bulky systems, and thus, not generally portable. NIR imaging apparatus may also cause patient discomfort because the apparatus may require a patient to be placed in certain positions or may require compression of patient breast tissue. Moreover, conventional NIR imaging apparatus and methods may be limited to imaging only fixed volumes or certain shapes of breast tissue.

In recent years, hand-held based optical imaging systems have been developed for clinical applications of the imaging technology. These hand-held based systems represent an alternative to the conventional bulky optical imaging systems. However, the hand-held optical imagers available may be limited by having only flat measuring probe heads that cannot conform to different tissue curvatures and/or may not be capable of performing three-dimensional (3-D) tomography studies. In addition, all these optical imagers typically employ single point illumination (e.g., using only a single existing light source or multiple existing light sources in which only a single source is activated at one time) and single/multiple point detection measurement geometries that limit the total data acquisition rates in a clinical environment. Because of the relatively slow data capture rates, patient discomfort and wait time may be further increased.

SUMMARY

The claimed method and system provides an optical imaging system and process that employs a flexible measuring probe head, simultaneous multiple point illumination and multiple point detection, and tracking facilities for associating location data with sensor data to enable generation of 3-D tomographic data for a target object (e.g., a tissue object or a phantom).

DRAWINGS

FIG. 1 illustrates a table of existing tumor diagnostic methods indicating principle of operation, advantages and disadvantages;

FIG. 10A illustrates a support plate having a plurality of pivotable plate sections;

FIG. 10B illustrates the support plate of FIG. 10A on a tissue surface;

FIG. 19 illustrates a block diagram of a method of producing tomograms of a target tissue object.

DETAILED DESCRIPTION

Figure 2:
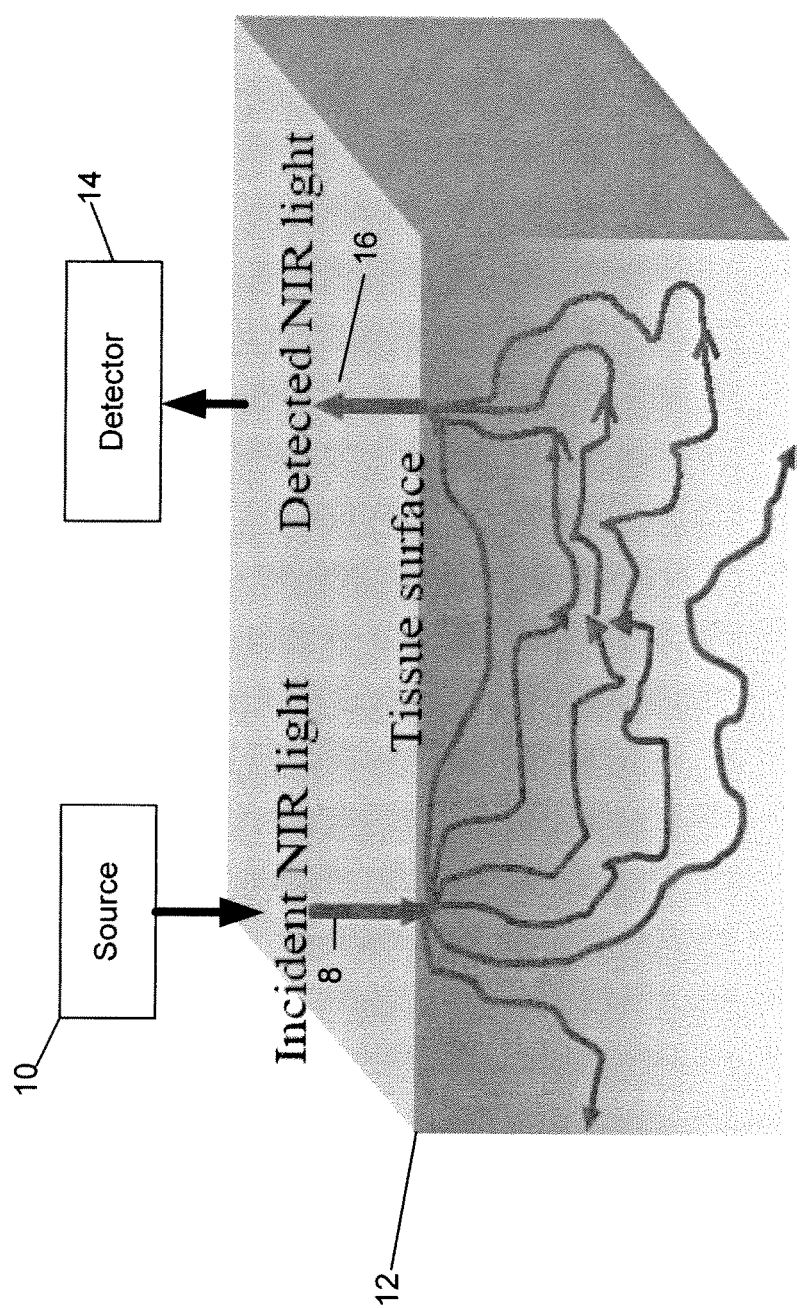
FIG. 2 illustrates a general optical imaging process.

FIG. 2 illustrates general principles behind an optical imaging process. Light 8 from a source 10 is projected on a target tissue 12 at a wave length of between 700-900 nm. The tissue 12 may minimally absorb the light 8 while reflecting and scattering a majority of the light. A corresponding light detector 14 may be positioned to measure characteristics of the reflected light 16, such as intensity, phase, or time delay.

Generally, when NIR light is launched onto a tissue surface, light propagates into the tissue and is minimally absorbed (in biological tissues, hemoglobin and water are least absorbent in the near-infrared spectrum) and preferentially scattered, allowing deep penetration of the light into the tissue and providing an opportunity for diagnostic imaging. The reflected light and/or trans-illuminated light (e.g., light that enters tissue at a first surface and exits the tissue at a second surface opposite the first surface) may be collected at a set of point locations on the tissue surface. From the collected reflected or trans-illuminated measurements, images of scattering ($\mu_s$) and absorption ($\mu_a$) coefficients of the entire tissue domain may be generated using appropriate light propagation models and reconstruction algorithms (to be discussed further below). Diffuse optical imaging enables researchers to translate the highly scattered light signals into clinically meaningful information about human tissue. For example, optical properties may be used to locate and identify physiological changes in the tissue that may indicate the existence and/or location of tumors.

Figure 3:
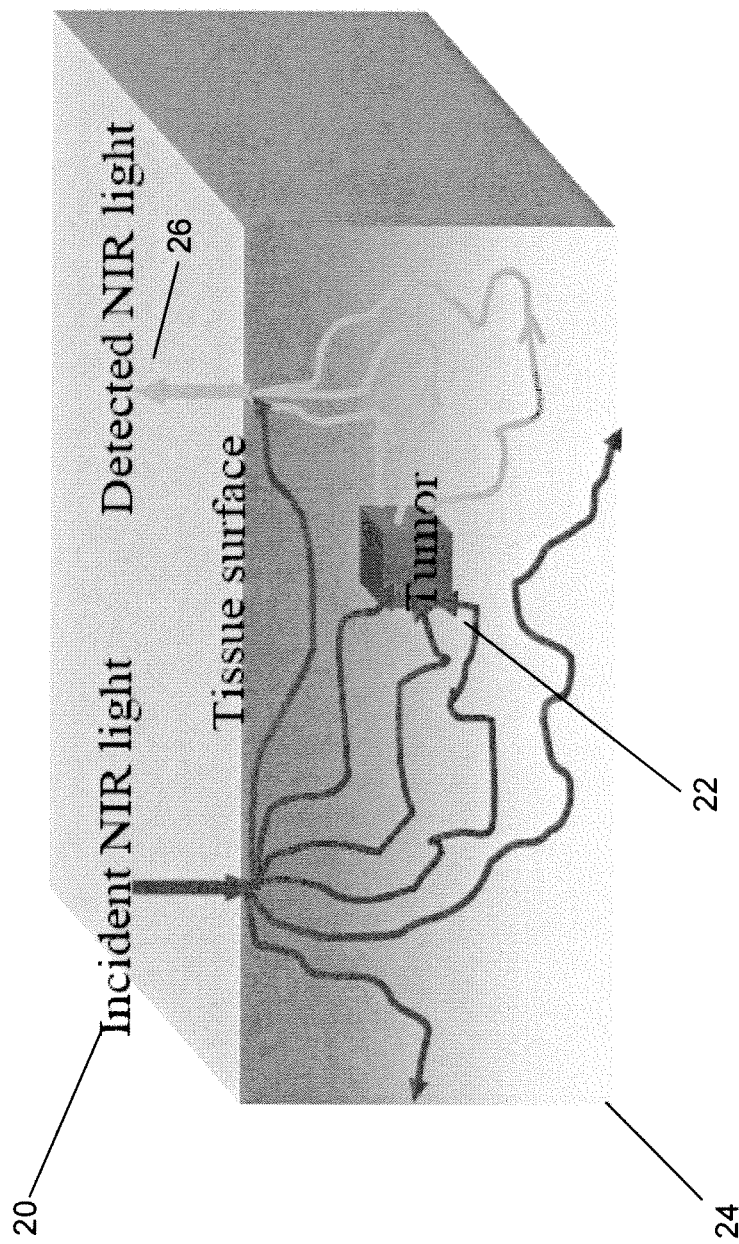
FIG. 3 illustrates a general optical imaging process in tumor diagnosis.

Differences in composition of the tissue may cause a difference in the light characteristics (e.g., in terms of reflected/trans-illuminated light intensity, phase, time delay, etc.) of the imaging data collected. This difference in light characteristics may be used to determine abnormal tissue growth. For example, optical imaging may be used to detect a breast tumor in a chemical environment by looking for two intrinsic cancer signatures: increased blood flow (as shown by the total hemoglobin concentration) and hypermetabolism (as shown by a drop in oxygen concentration). As illustrated in FIG. 3, when NIR light 20 encounters an angiogenic (growth of blood vessels from surrounding tissue to solid tumors) region 22 of a breast tissue 24, light may be absorbed based on the different concentrations of hemoglobin in that area of the breast, thus providing endogenous contrast between normal and tumor tissue. The difference in light characteristics of the collected diffused light 26 may reflect the difference in absorption and/or scattering arising from this angiogenic region 22.

To detect lesions smaller than about 0.5 cm (in diameter) external contrast agents may need to be used in order to improve the optical contrast between normal and diseased tissues in a process known as fluorescence enhanced optical imaging. Fluorescence-enhanced optical imaging involves the administration of exogenous fluorescent contrast agents that specifically bind to target tissue (e.g., tumor tissue) and that are excitable in the NIR wavelength range. The external fluorescent contrast agents molecularly target the metastatic cancer cells within the breast tissue and enhance the optical contrast between the cancerous cells and the background breast tissue.

Figure 4:
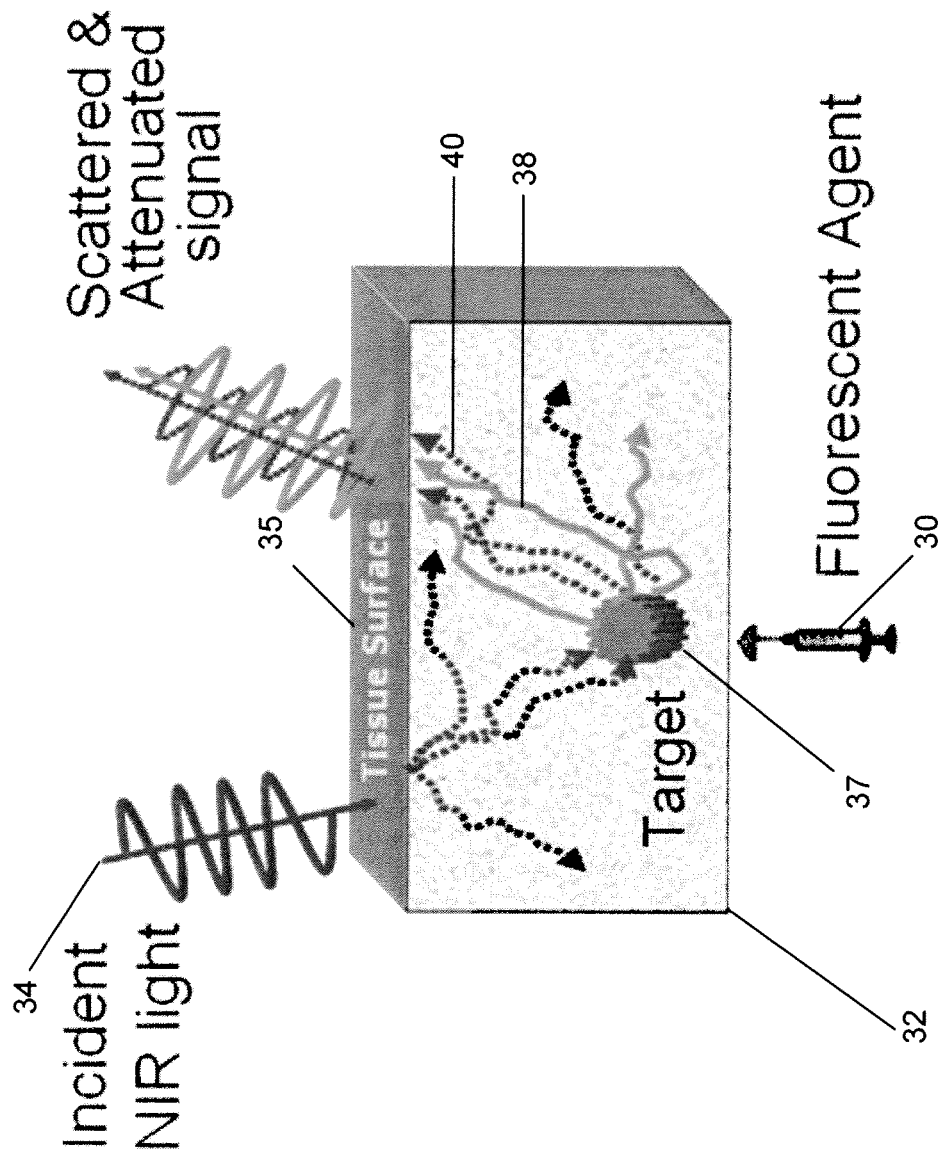
FIG. 4 illustrates a fluorescence-enhanced optical imaging process.

FIG. 4 illustrates a fluorescence-enhanced optical imaging process. In a fluorescence-enhanced optical imaging process, a target specific florescent contrast agent 30 may be injected into the tissue 32. When NIR light 34 (that is between 700-900 nm wavelengths) is launched at the tissue surface 35, the minimally absorbed and preferentially scattered excitation photons propagate deep into the tissue 32. Upon encountering a fluorescent molecule 37 (e.g., found at the site of target tissue substructure), the photons excite the fluorescent molecule 37 from its ground state to a higher orbital level. After residing at the higher energy orbital for a period (known as the fluorescence lifetime), the fluorescent molecule emits a fluorescent signal 38 at a greater wavelength than the incident NIR light 34. The emitted fluorescent signal 38 along with the attenuated excitation signal 40 (which is at the same wavelength as incident light) propagates back through the tissue surface where it is detected. At a detection site (not shown in FIG. 4), appropriate optical filters may be used to separate the fluorescence signal from the attenuated excitation signal to provide relevant light characteristic data.

Imaging Data Signal Processing

Three distinct measurement techniques may be used to process the collected light characteristic data in optical imaging. These techniques include continuous wave, time-domain (TD), and frequency-domain (FD) based imaging. Each of these measurement techniques has advantages and disadvantages, and the selection of the appropriate technique largely depends on the specific application and requirement.

Continuous wave measurement technique uses steady state light of constant intensity on the tissue surface and measures the attenuated intensity of the trans-illuminated and/or reflected light. In continuous wave based fluorescent optical imaging the NIR light attenuates due to absorption and scattering in the tissue medium. Upon encountering the florescent molecule, a steady state florescent signal is emitted, which attenuates before it is detected at the tissue surface. Continuous wave-based imaging instrumentation is relatively simple and involves low-cost optical components. The major disadvantages of continuous wave measurement technique include difficulty in resolving tissue absorption from scattering and inability to image the fluorescence decay kinetics. When independent measurements of tissue optical properties (i.e. absorption, scattering or fluorescence lifetime) and/or depth information are required, the use of TD or FD measurement techniques may be necessary.

Time domain (TD) measurement techniques illuminate tissue with ultra fast (e.g., in the femtosecond to picosecond time range) photon pulses and resolve the arrival of the photons as a function of time at different locations around the tissue boundary. In a TD-based fluorescence optical imaging process the excitation light pulse broadens and attenuates as it travels through the scattering medium. Upon encountering a fluorescent molecule, a fluorescent light pulse is emitted, which broadens and attenuates as it propagates in the tissue medium. This broadened pulse of fluorescent light is further broadened and attenuated due to absorption and scattering in the tissue medium, before it is detected at the tissue surface using, for example, fluorescence optical imaging.

The TD measurement technique may provide better depth information compared to a continuous wave measurement technique. Although TD based measurements provide a wealth of information that may be used to map optical properties of tissues, TD measurement techniques may be limited by their large signal-to-noise ratio (SNR) range, which may require significant data acquisition times compared to CW and FD measurement techniques.

In FD-based fluorescence optical imaging, modulated excitation light is launched onto the tissue surface and the modulated fluorescent signal is detected at the tissue surface in terms of amplitude and phase shift. Measurements of the light intensity and the phase shift of the photon wave-front are obtained with respect to the source light information about the tissue optical properties and fluorochrome distribution. Frequency domain measurement technique may be preferable over TD measurement technique due to its inexpensive instrumentation. In addition, the steady-state FD measurements in terms of amplitude and phase shift are minimally corrupted by ambient light, since the instrument detects only a modulated signal. Thus, the FD instrument automatically acts as a filter for ambient light rejection, which is an advantage of FD measurement techniques over continuous wave or TD measurement techniques. However, FD measurement techniques require frequencies of several hundred MHz or higher to achieve depth information that may be difficult to obtain using continuous wave technique. In practice, usually a single frequency may be employed, and the phase shift may be used to estimate the mean time of flight of the photons. However, data obtained at multiple frequencies may improve FD imaging performance and may be become equivalent to TD data via the inverse Fourier Transform.

Source and Detector Configurations for Optical Imaging

NIR based imaging approaches, whether based on endogenous or exogenous contrast, involve trans-illumination and/or reflection measurements. These measurements represent the light propagation between light sources and detector sensor pairs, and are based on excitation illumination and excitation/emission detection. Generally, trans-illumination is the shining of a light through a target tissue, such as breast tissue, to observe the absorption pattern from the opposite side of the tissue medium. Reflection measurements involve observing light reflected off a tissue surface from the same side as the incident light.

Generally, existing optical imaging configurations for arranging sources (for providing incident/excitation signals) and detectors (for collecting reflected and/or trans-illuminated NIR signals, fluorescence or non-fluorescence signals) may be broadly categorized into projection shadow, circular, and sub-surface/reflective configurations.

Figure 5:
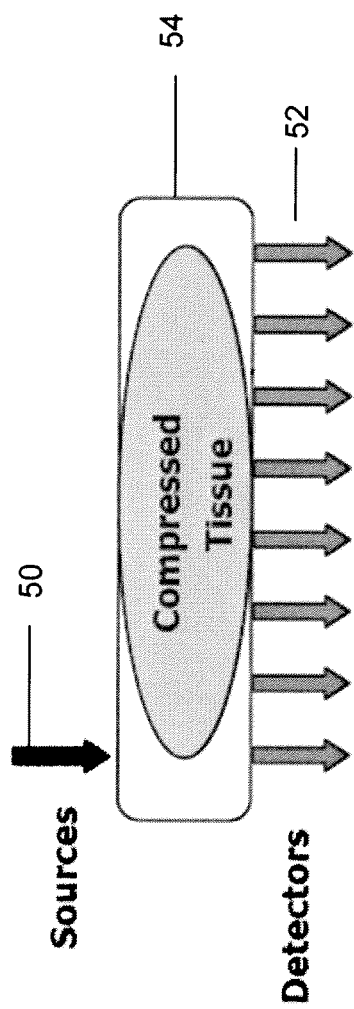
FIG. 5 illustrates a projection-shadow optical imaging process.

FIG. 5 illustrates a projection-shadow optical imaging process. Projection-shadow imaging involves collecting trans-illuminated light from the tissue object. Trans-illuminated light may refer to light that traverses a surface(s) of a tissue. In trans-illumination method, sources 50 and detectors 52 are placed on opposite sides of breast tissue 54. In this geometry, single/multiple sources may be deployed on an opposite plane that is parallel to the detector plane that has single/multiple detectors. Optical properties of the three dimensional tissue are obtained between the source and the detector planes. This method generally requires compression of the target tissue. The compressed tissue configuration may be analogous to x-ray mammography, and may be disadvantageous due to patient discomfort caused by tissue compression and due to limited information obtained for the entire breast tissue.

Figure 6:
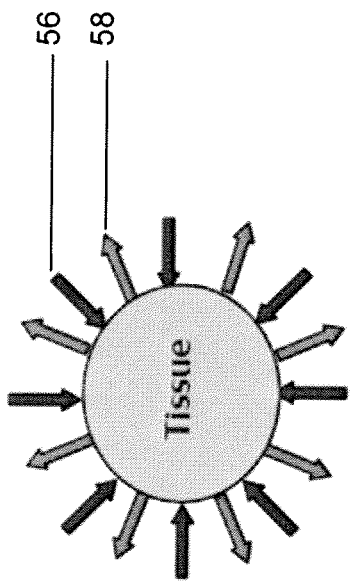
FIG. 6 illustrates a circular imaging process.

FIG. 6 illustrates a circular imaging process, wherein both the reflected and trans-illuminated light is collected along a circular circumference of the tissue. In this configuration, multiple sources 56 and detectors are disposed about the circular circumference of the tissue. The circular configuration may be minimally discomforting to a patient, but is limited by the bulky and non-portable size of the apparatus.

Figure 7:
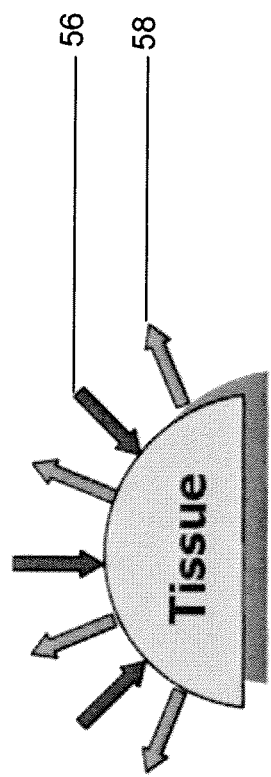
FIG. 7 illustrates general sub-surface imaging.

FIG. 7 illustrates sub-surface imaging, which may involve collecting reflected and/or trans-illuminated light using multiple sources 56 and detectors 58. This configuration requires no tissue compression, and may be designed to mimic a hand-held imaging probe. To date, all the optical imaging systems and hand-held probes developed using the sub-surface imaging configuration are designed to only collect reflected light using flat measurement probe heads.

Three-dimensional tomography studies may be performed using the projection-shadow or the circular imaging configuration. However, 3-D tomography studies have been limited by the sub-surface configuration because of the limited depth information obtainable in the absence of trans-illuminated measurements, and also from lack of co-registering the source and detector locations on the target tissue object that is imaged.

Illumination Area

Figure 8B:
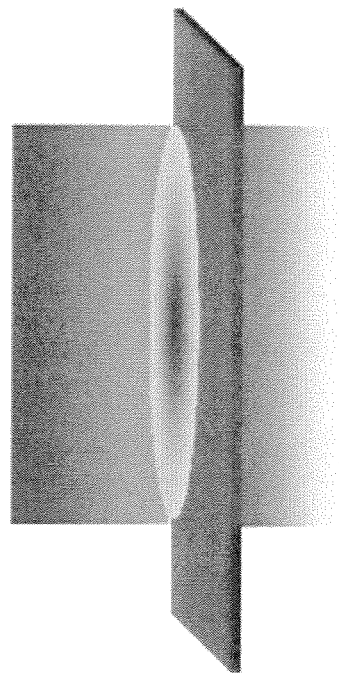
FIG. 8B illustrates a wide-area illumination.
Figure 8A:
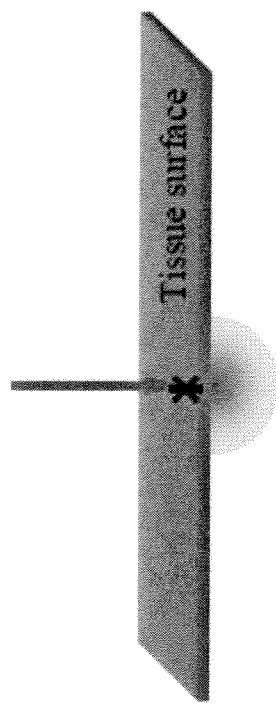
FIG. 8A illustrates a point-wise illumination.

There are essentially two methods of illuminating the tissue surface; wide-area illumination as illustrated in FIG. 8B and point-wise illumination as illustrated in FIG. 8A. In wide-area illumination the intensity is typically not uniform (e.g., the intensity may typically be relatively higher at the center than at the edges of the region). To date, most optical imaging studies have typically been performed using sequential single point illumination (FIG. 8A) and sequential or simultaneous multiple point detection measurement techniques. Although the data acquisition rates are enhanced upon using simultaneous point detection techniques, in terms of illumination geometries, most optical imaging studies have been limited to using sequential single point illumination of the tissue surface during imaging. For sub-surface optical imaging, a point illumination system vastly reduces variations in intensity on the imaging surface overcoming one of the limitations posed by wide area illumination as shown in FIG. 8B. However, illumination by excitation light from a single point interrogates a relatively small portion of tissue volume 8A, thus increasing the total data acquisition times in order to image the entire tissue volume. In addition, sequential single point illumination may also provide insufficient light intensity to perform tomographic studies on large tissue volumes with greater penetration depth (since optical signals decay exponentially with distance). Weak optical signals are usually dominated by noise, thus impacting the measurement precision and accuracy, and eventually hindering the accurate reconstruction of the target location and size. Thus, sequential single point illumination not only may impact the total imaging time (due to small portion of tissue volume illumination), but may also be insufficient to generate a detectable NIR signal from small and/or deeply located targets.

The imaging method and system embodiments described herein use various combinations of source-detector configuration, illumination, and signal processing to provide an improved hand-held optical imaging probe that may be used for 3-D tomography studies, with reduced total imaging time, and ability to image any tissue curvature.

Probe Head

Figure 9A:
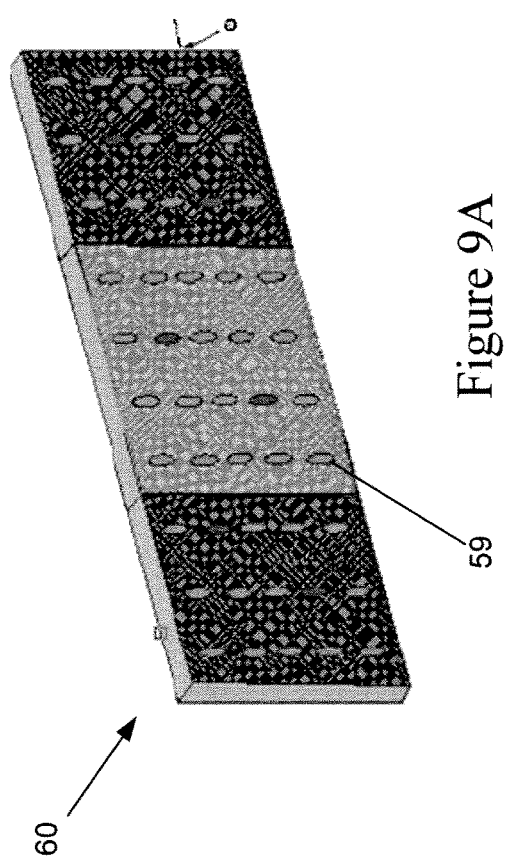
FIG. 9A illustrates a support plate that may be used in a probe head.

FIG. 9A illustrates a support plate 60 that may be used in an embodiment of an improved NIR imaging apparatus and method to arrange a plurality of fiber optic cables (the term fiber optic cable(s) is used interchangeably with optical fiber cable(s) herein). In particular, first ends 59 of fiber optic cables may be terminated on the support plate 60 in a direction transverse the plane of the support plate 60. In this embodiment, some optical fibers may be used as optical source fibers to carry light from a light source to a terminal end at the plane of the support plate or as optical detector fibers that receive and collect light at the plane of the support plate and channel the received light along their lengths to a detector or a plurality of detectors.

FIG. 10A illustrates that the support plate 60 may be divided into three planar sections or plate sections 61, 62, 63. The planar sections 61-63 may be pivotably coupled to one another. In the embodiment of FIG. 10, a first plate 61 may be pivotably coupled at an edge 66 with a second plate 62. The second plate 62 may be pivotably coupled to a third plate 63 at another edge 67 of the second plate 62. In this embodiment, the support plate may be conformed, along the pivotable edges 66 and 67, to a surface 68 of a three dimensional target object, such as a breast tissue or any other body part, as illustrated in FIG. 10B. This curved geometry of the optical probe embodiment enables improved contact of the source-detector array on a three dimensional object and thus provides greater accuracy on the tissue data collected.

Figure 11:
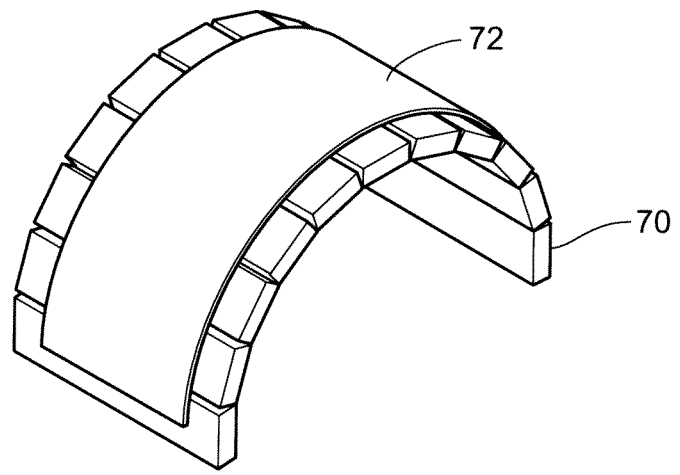
FIG. 11 illustrates another embodiment of a support plate comprising a plurality of plate sections.

FIG. 11 illustrates another embodiment where the support plate 60 may be divided into a plurality of plate sections 70 that may be connected together by pivotably coupling along their edges, or by using any flexible sheet of material 72, such as an aluminum or other appropriate material. In this manner, a greater amount of surface contact to the target object may be provided based on the plurality of discrete sectional plates 70. Alternately, a flexible sheet of material (or combination of materials) without any plurality of sectional plates can be used directly, upon which the first ends of the optical fiber cables can be connected at various locations via drilled holes.

Figure 12:
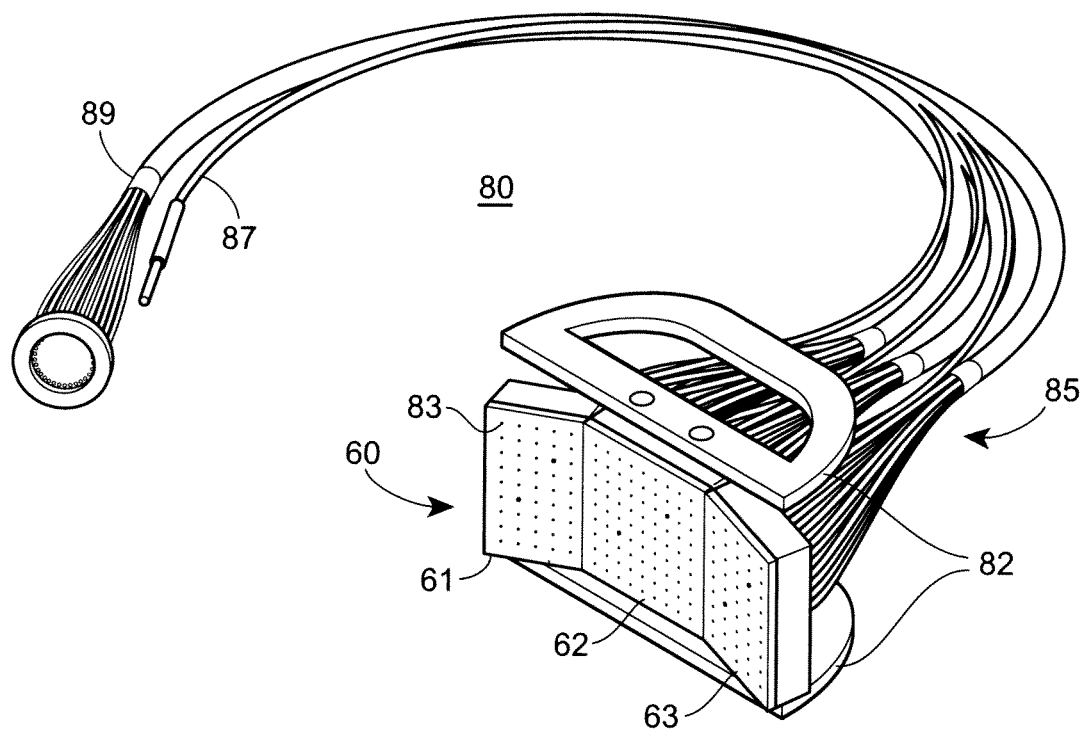
FIG. 12 illustrates an optical imaging probe using the support plate of FIGS. 10A and 10B.

FIG. 12 illustrates an optical imaging probe 80 using the support plate 60 of FIGS. 10A and 10B. The support plate 60 having planar sections 61-63 may be coupled to a support frame 82. First ends 83 of optical fibers 85 (including optical source fibers and optical detector fibers) may be terminated at the support plate 60. Optical source fibers may be arranged in a first bundle 87 for coupling to a light source. Optical detector fibers may be arranged in a second bundle 89 for coupling to a detection system or detection module.

Figure 9B:
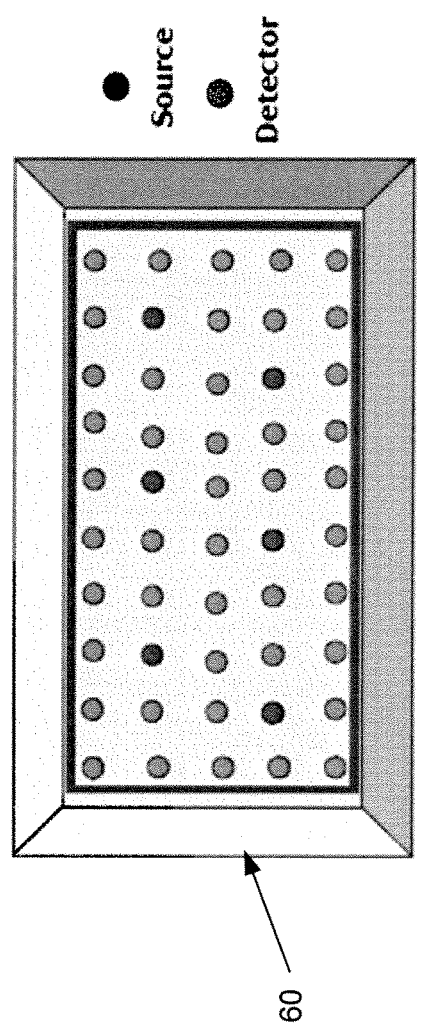
FIG. 9B illustrates a detailed view of the support plate for FIG. 9A.

In one embodiment, simultaneous multiple point illumination and simultaneous multiple point detection technique using optical fibers may be used. Using the support plate 60 of FIG. 9A, where the face of plate is enlarged in FIG. 9B, a plurality of optical source fibers ends may be disposed on the plate 60 at locations indicated by dark circles. Ends of optical detector fibers may be terminated at the plate and positioned around the optical source fibers ends as indicated by light circles in FIG. 9B. The optical detector fibers may receive and collect light at the plane of the support plate and channel the received light along their lengths to a detector or a plurality of detectors.

In one embodiment, each of the optical source fibers may be adapted to simultaneously launch the NIR light from a light source onto the tissue object surface. In another embodiment, each of the optical source fibers may sequentially emit NIR light from a light source onto the tissue object surface. Moreover, the light may be emitted from each of the optical source fibers at substantially the same intensity (preferably) or even different intensities. In one embodiment, the intensity difference between any one of a set of optical source fibers disposed on the planar support frame may be within three percent (sometimes higher depending on the application). If the simultaneous light intensities are significantly different, they may be accounted for in mathematical models representing light propagation in tomography related studies.

Figure 13:
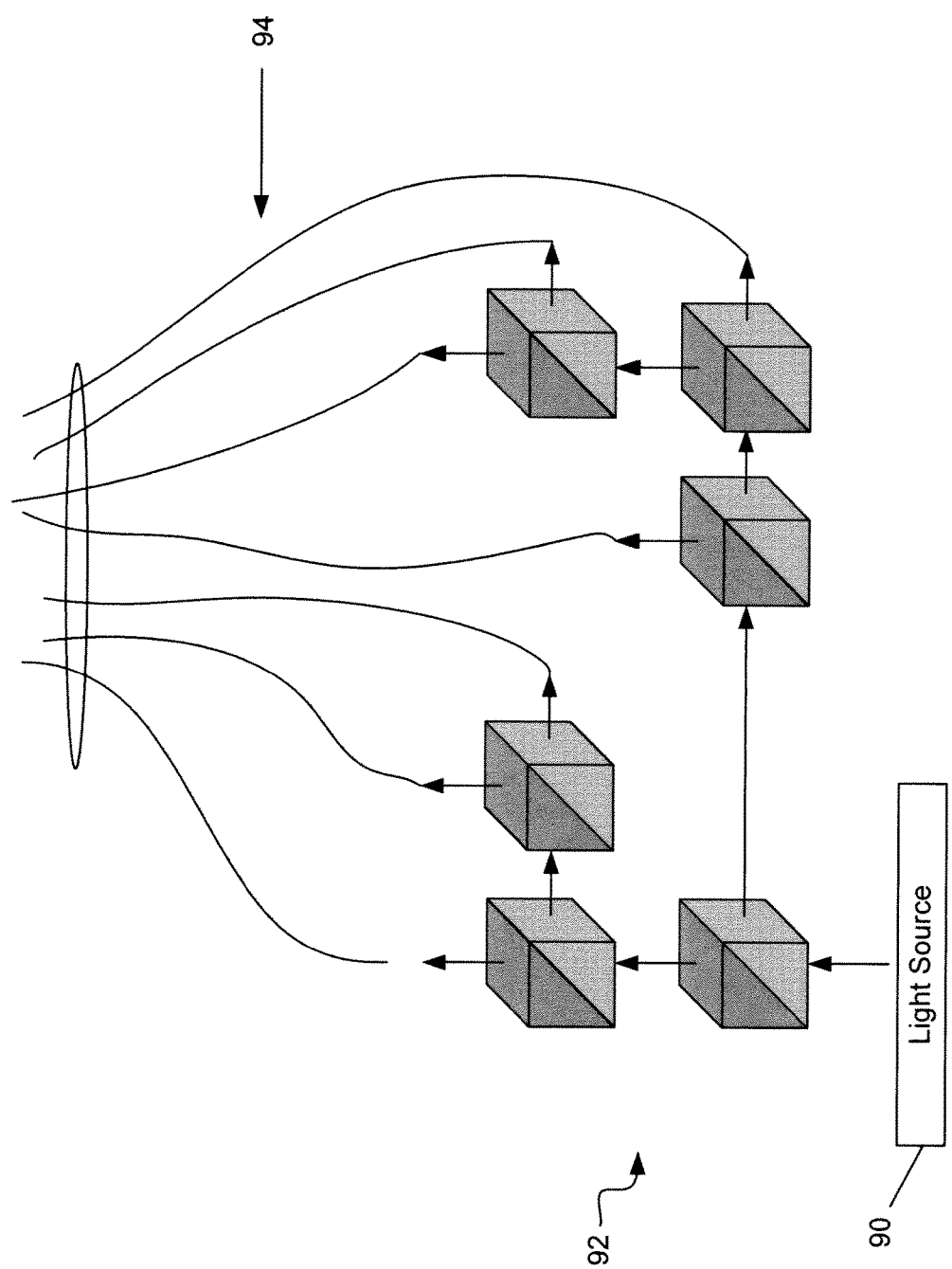
FIG. 13 illustrates an embodiment of a system using optical dividers to simultaneously illuminate a plurality of optical source fibers.

FIG. 13 illustrates an embodiment of a system for simultaneously emitting a plurality of simultaneous light beams at the support plate at substantially the same intensity via a set of optical source fibers. In this embodiment, a light source 90 may be used to generate light that is applied to a plurality of optical dividers 92. In one embodiment, the light source 90 may be a laser. In other embodiments, the light source 90 may be any suitable light source for producing a beam of light at necessary intensities. The optical dividers 92 may be prisms that are aligned in a manner to provide the substantially equal or unequal (but pre-determined) beams of light. In one embodiment, this may require aligning the prisms to provide a total variance in light intensity between the beams of less than about three percent. The plurality of light beams resulting from the optical division may be channeled into ends of a plurality of optical source fibers 94. The second ends of the plurality of optical source fibers 94 may then terminate at the support plate 60 described above (e.g., ends 83 as illustrated in FIG. 12).

Figure 14:
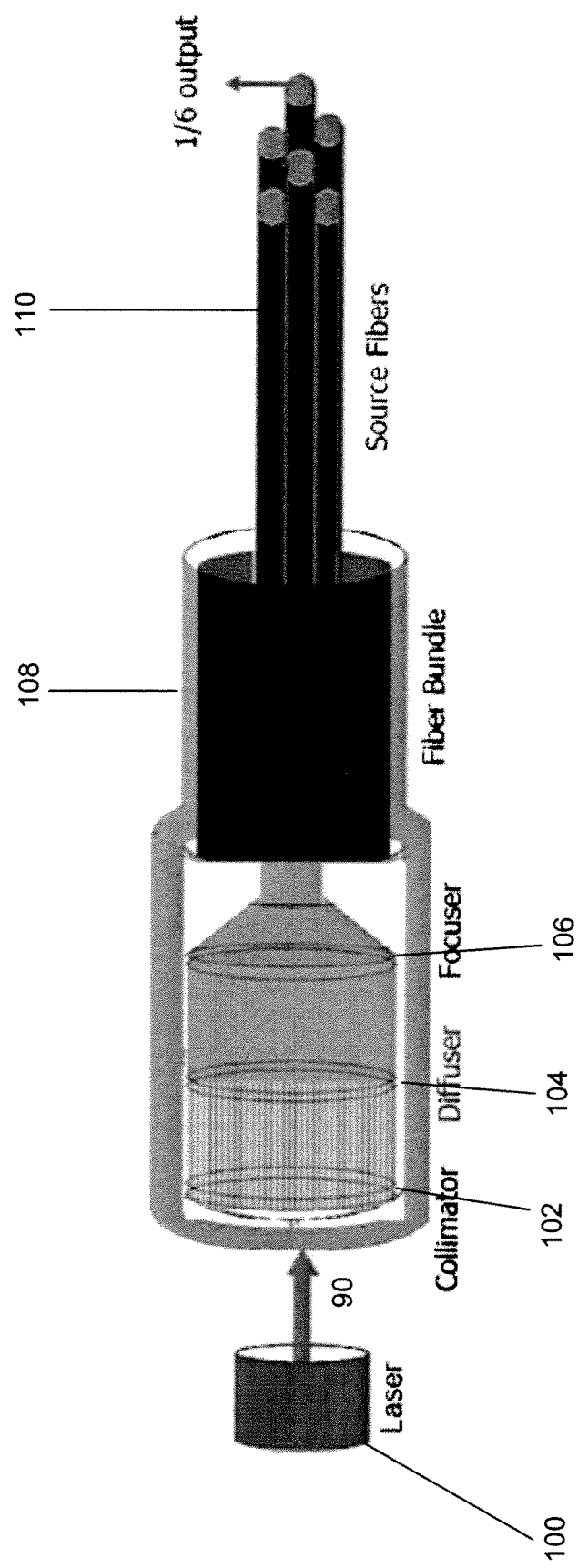
FIG. 14 illustrates an embodiment of a system that provides a plurality of light sources using different optical lenses.

FIG. 14 illustrates another embodiment of a system for simultaneously emitting a plurality of light beams at the support plate 60 at substantially the same intensity via the set of optical source fibers. In this embodiment, a laser 100 may be used as a light source (although other light sources for providing light to the system may be used). The laser light may be collimated at a collimator 102. In some embodiments, the collimator 102 may be optional. Collimated light output from the collimator 102 may then be channeled to a diffuser 104 for evenly spreading the collimated light over a particular surface area. In this embodiment, the diffuser 104 spreads the collimated light over the input surface of a focuser 106. The focuser 106 may be selected to concentrate collimated light onto first ends of a bundle 108 of optical source fibers. In one embodiment the diffuser 104 and/or focuser 106 may be optional. The optical source fibers 110 may then terminate at seconds ends at the support plate 60 (e.g., ends 83 as illustrated in FIG. 12).

Sensor and Detector System

Figure 15:
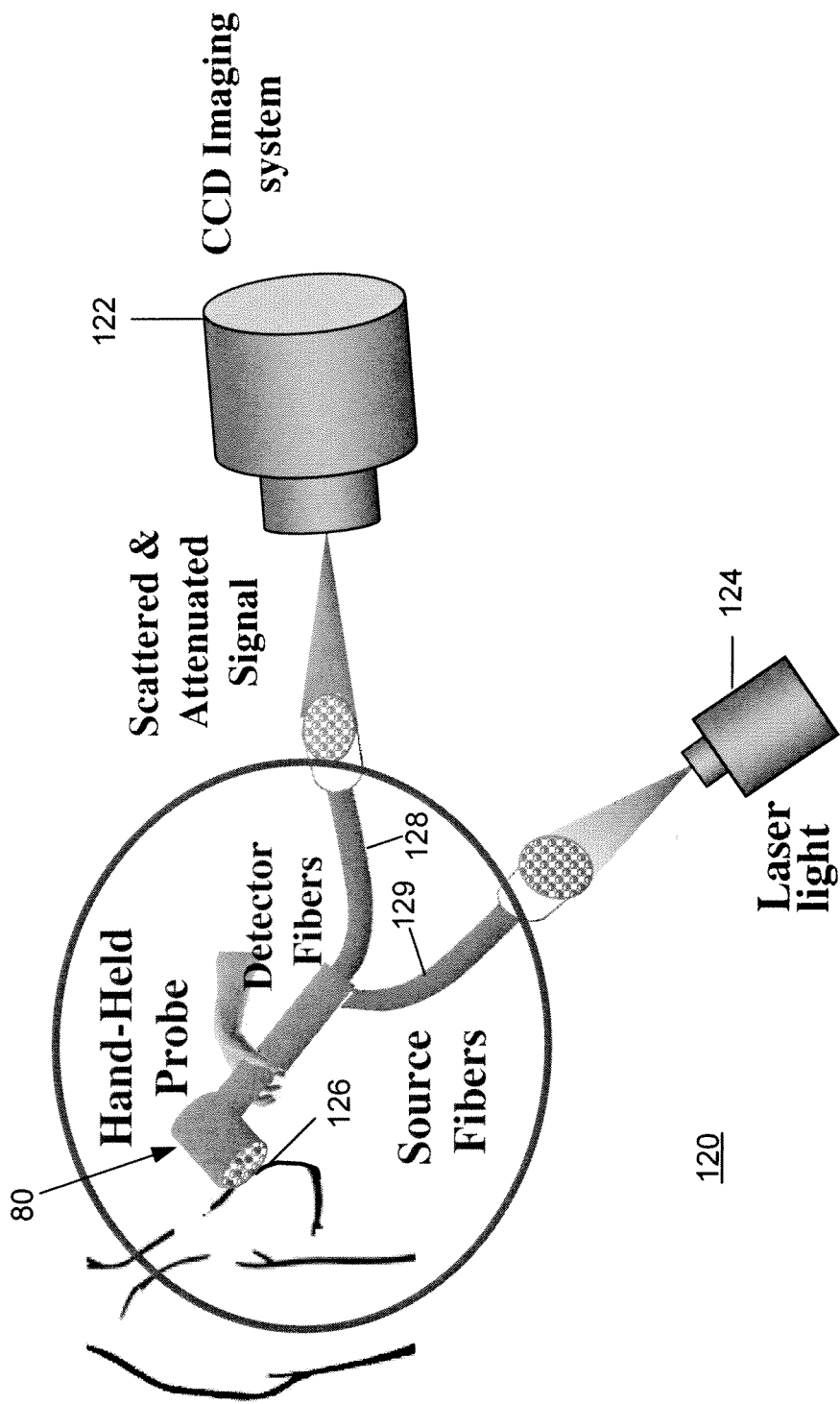
FIG. 15 illustrates a optical imaging system 120 embodiment using the probe of FIG. 12.

FIG. 15 illustrates an optical imaging system 120 embodiment using the probe 80. In this embodiment, a fluorescence-enhanced or non-fluorescence diffuse optical imaging process may be used. A frequency-domain intensified CCD (ICCD) detection module 122 may be coupled to the hand-held optical probe 80. The detection module 122 may be any CCD sensor or other detector such as photo-multiplier tubes (PMT), avalanche photo diodes (APD), or silicon photo diodes. These detectors may be used individually or in a plurality to detect light. If a plurality of the detectors are used, the detectors may be activated sequentially or simultaneously. The detection module 122 may be configured to operate as a time-dependent (FD or TD) and/or as a time-independent (CW) detection system. The detector system may operate in conjunction with a light source 124 using TD, FD, or CW approaches. While FIG. 15 illustrates that the light source 124 is a laser source, any other light source capable of providing the appropriate light characteristics may be used. As illustrated in FIG. 15, light from light source 124 may be projected on to a target tissue surface 126 via optical source fibers 129. The hand-held probe 80 may collect NIR signals from different points on the tissue boundary surface 126 via optical detector fibers 128, where the signals may be simultaneously processed using the gain-modulated ICCD detector 122 for an enhanced data acquisition rate. A homodyne technique may be implemented in the system 120 where the laser source 124 and the detector 122 are modified at the same frequency (e.g., in the MHz range). Data acquisition rates of the homodyned frequency domain measurements may depend on the number of phase delays between the frequency synthesizers modulating the image intensifier and the laser diode, the number of repeated images averaged to acquire phase-sensitive images, the integration or exposure time of the CCD to obtain each image, and the degree of data binning downwards from a pixelated image in the CCD. The combination of the above variables may be assessed to determine the data acquisition scheme with minimal measurement time, reduced measurement errors, and maximum resolution of the optical images. In one embodiment, the frequency-domain measurements detected by the detection module 122 may be based on the heterodyne technique, where the modulation frequencies at the laser source 124 and the detector 122 are not the same.

Figure 16:
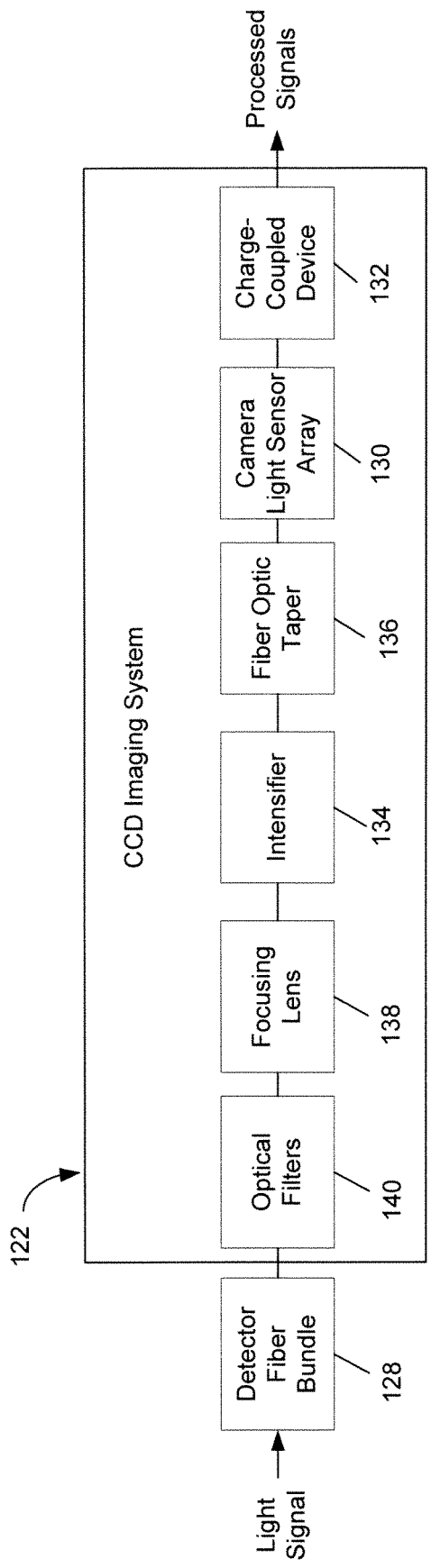
FIG. 16 illustrates a detection system using a charge-coupled device.

FIG. 16 illustrates further details of the CCD imaging module or system 122. The CCD imaging system 122 may be built using a custom 16-bit CCD camera that includes a photo-detector array 130 for transforming light signals into corresponding electrical signals and a charged-coupled device 132 for processing the electrical signals. The photo-detector array 130 and charge-coupled device 132 may enable higher frame transfer capability to enhance image acquisition and storage rates. The photo-detector array 130 may be fiber optically coupled to a near infrared (NIR) sensitive image intensifier 134 via a fiber optic taper 136. The image intensifier 134 may be included in the CCD system to amplify weak light signals at MHz range. The NIR-sensitive image intensifier 134 (e.g., a conventional filmed or filmless tube) may generally work to reduce image retention effect and to increase sensitivity to weak NIR (both fluorescence and non-fluorescence) signals. A custom-built fiber optic taper 136 may be used to interface the output of the intensifier to the photo-detector array 130 to improve the coupling efficiency of image intensifier. In a frequency-domain based imaging system, the image intensifier may be modulated at MHz range, unlike the CCD camera when used in the absence of coupled intensifier.

The optical detector fibers in bundle 128 may be coupled to optical filters 140 and a focusing lens 138, where the focusing lens 138 then outputs light signals to the intensifier 134. Different optical filter combinations (e.g., interference, long pass, band pass, holographic, etc.) may be used to isolate and extract light signals at particular wavelengths of interest and to remove signals at other wavelengths. In the case of fluorescence-enhanced optical imaging, use of an appropriate optical filter combination may help minimize the excitation leakage that prevents the detection of weak and low intensity fluorescence signals arising from deep and/or small targets.

Mapping of Sensor Data to Location Data to Produce a Tomogram

In both modeling and image reconstruction, a region of interest(s) (e.g. 2-D or 3-D tissue object or phantom) may be divided into discrete 2-D or 3-D elements. Due to the limited surface area of the probe head, sensor data is captured only for a portion of the region of interest at one time. To obtain three dimensional visualization of a large region of interest, each time the probe is moved, its position and orientation may be monitored and registered or mapped. As used herein, registration refers to the mapping of sensor data for a particular region onto to a map of the entire region of interest(s). Generally, registration provides 3-D location and orientation data for the sensor data. For example sensor data captured during a first period at a first position of the probe may be mapped to a corresponding first position of a map of the entire region of interest. To implement self-registration or co-registration of the sensor data for the region of interest, an ultrasonic tracking system may be used to monitor the location of the probe.

Acoustic trackers that determine probe location via sound may be appropriate for an optical imaging system because acoustic receivers may be small, lightweight, and inexpensive. Moreover, unlike magnetic trackers, acoustic trackers may not suffer from distortion in the presence of magnetic fields and may not require specially designed environment for operation. In one embodiment, the optical imaging probe 80 of FIGS. 12 and 15 may incorporate a 3-D tracking device that uses acoustic signals to monitor the 3-D position and orientation of the optical imaging probe.

Figure 17:
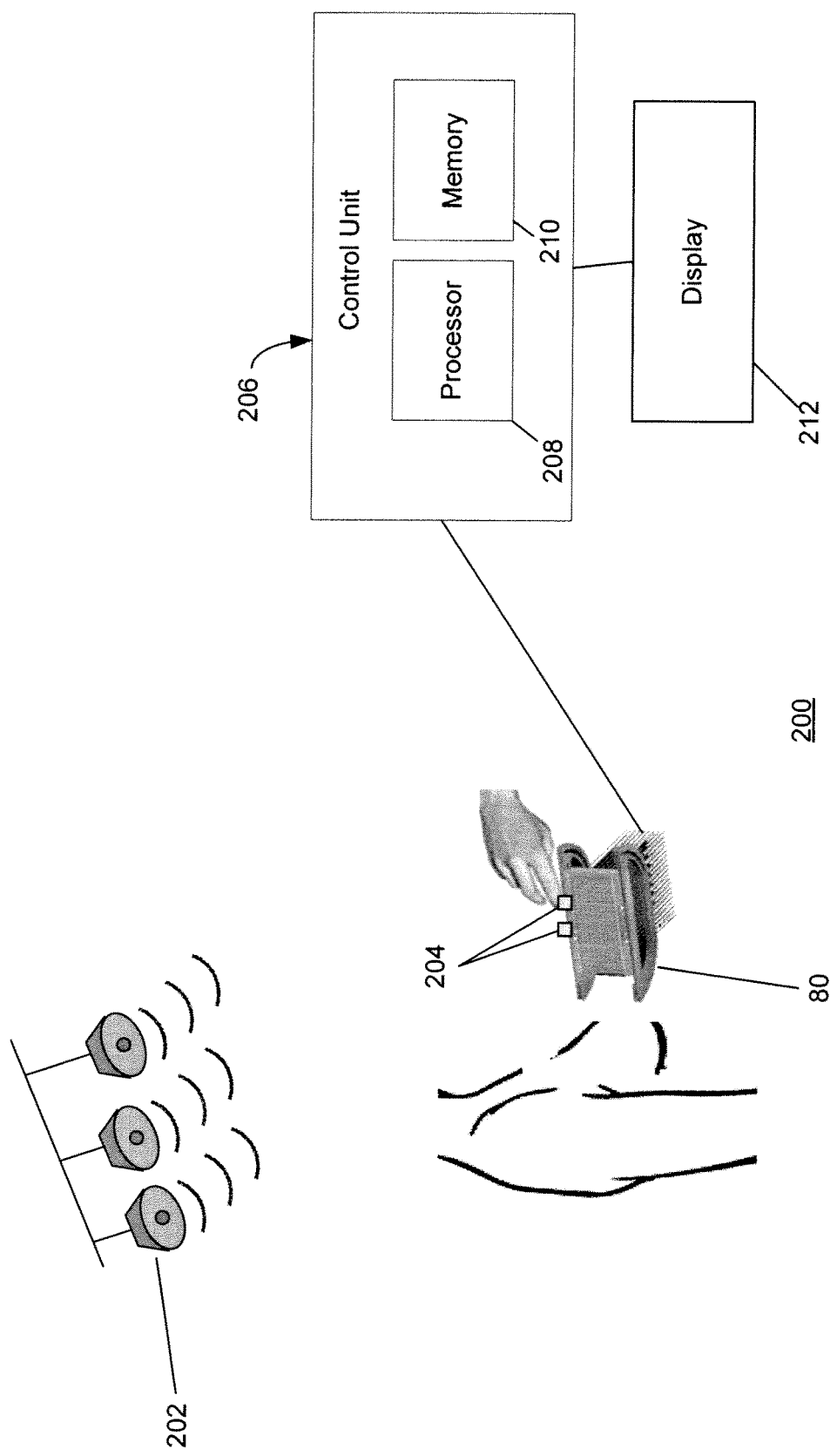
FIG. 17 illustrates an ultrasonic tracking system that may be used in conjunction with an optical imaging probe.

FIG. 17 illustrates an ultrasonic tracking system 200 that may be used in conjunction with the optical imaging probe 80 described above. The tracking system 200 may comprise a set of transmitters 202, a set of receivers 204 coupled to the optical imaging probe 80, and a control unit or processing unit 206. The processing unit 206 may be a computing device having a processor 208 and a memory 210, as known by those skilled in the art. The processing unit 206 may be coupled to a display device 212 for displaying images. In the embodiment illustrated in FIG. 17, the set of transmitters 202 may be located at a fixed location with respect to the receivers that are coupled to the imaging probe. In an alternative embodiment, the transmitters may be coupled to the imaging probe while the receivers may be placed at a fixed location with respect to the transmitters.

The set of transmitters 202 of FIG. 17 may comprise several speakers that send acoustic signals (e.g., in the ultrasonic range) to the receiver 204. The set of receivers 204 may be coupled to the hand-held probe 80 by, for example, embedding several microphones on the surface of the hand-held probe 80. The microphones may sample signals from the set of transmitters at a constant rate. The control unit 206 may decode signals from receivers in the following manner.

The speakers 202 may emit ultrasonic pulses at regular intervals. The receivers 204 may detect the pulses and record their times of arrival and from that information, the computing device 206 may be used to determine the position of the hand-held probe with respect to the fixed transmitter location. Because the times of transmission of the pulses are known, the times of flight of the pulses may be computed. This flight time may then be used to compute the distances between the speaker and sensor by multiplying the times of flight by the speed of sound in air. These distances and the known positions of speakers may provide sufficient information for computing the position and orientation of the hand-held probe.

Figure 18:
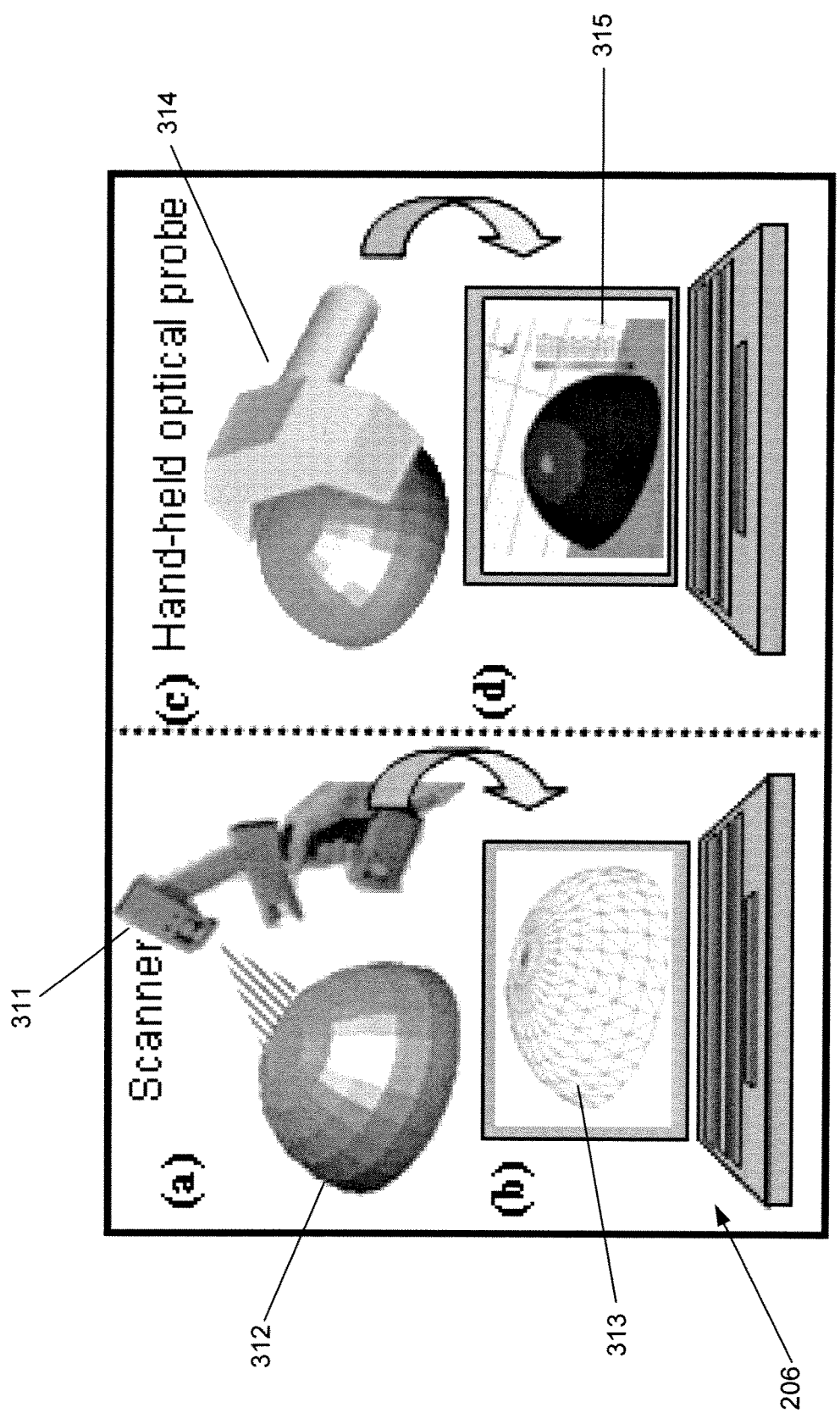
FIG. 18 illustrates a process embodiment of an optical imaging system.

FIG. 18 illustrates a possible embodiment of the process of obtaining 3-D tomographic relevant sensor data using a self-registering (automatic registering) hand-held probe based imaging system. A three-dimensional optical scanner 311, as known in the art, may be used on the target object 312 (without any contact) to provide a 3-D surface image of the target object, which can be volume rendered and discretized using appropriate meshing software, as known in the art. In one embodiment, the volume rendering process may involve generating a three-dimensional mesh of point coordinates or point locations sub-surface to the rendered 3-D surface image (e.g., for the entire volume of the target object 312). The 3-D mesh of the target object 313 may be displayed on computing device 206. A probe 314 for collecting sensor data, such as the optical imaging probe described above, may then be traced over the target object 312 to obtain sensor data. The 3-D location map of the probe 314 with respect to the 3-D mesh of the target object 313 may be obtained using the tracking system 200. In one embodiment, the computing system 206 may be programmed (e.g., using appropriate software and algorithms) to receive sensor data from the probe for a time period, receive probe position data from the tracking system 200 for the time period, and map the sensor data to appropriate mesh locations on the 3-D mesh based on the position data. In this manner, the location data and the sensor data collected over a region may be mapped to the corresponding region on the 3-D mesh surface 313 to generate a co-registered map sensor and location data 315. The computing device 206 may register or map sensor data with respect to a reference position arbitrarily chosen on the 3-D mesh of the target object 313. The computing system 206 may be further programmed to process the sensor data before and/or after mapping to the mesh depending on a particular application of the sensor data. This map of sensor data to location may then be transformed into a 2-D and/or 3-D tomogram using appropriate algorithms. These tomograms may include reconstructions of subsurface structures within the target object. The subsurface structures may include abnormal tissue such as tumors.

FIG. 19 illustrates a process embodiment for producing tomograms of a target tissue object. At block 301, a three-dimensional scanner and appropriate meshing software may be used to render a three-dimensional map (e.g., a mesh of point locations) of the target three-dimensional tissue object. At block 302, a probe may be traced over the target tissue object. As the probe is traced over the target tissue object and sensor data is recorded, the position of the probe may be tracked 303 and recorded using, for example, the tracking system described above. Timed sensor data may then be mapped to a location on the 3-D map 304. In one embodiment, a computer, such as computer 206, may be programmed to receive sensor data from the probe at a period of time, to receive location information from the tracking system, and map this data to corresponding points on the 3-D map or mesh of the target object. In this manner, a location or coordinate value is associated with the timed sensor data. At block 305 the sensor data may be processed along with the coordinate or location information associated with the sensor data to produce a tomogram of the three-dimensional tissue object using appropriate inverse algorithms.

It should be noted that while one embodiment of the process illustrated in FIG. 19 is used with an optical imaging probe as described above, the process may be used with other types of probes and sensors to generate a tomographic reconstruction of subsurface structures. For instance, hand-held imaging systems are available in other imaging modalities (e.g. ultrasound, gamma imaging, and electrical impedance tomography), apart from optical imaging. However, to date none of these hand-held imagers (optical or other modalities) are capable of providing 3-D tomographic relevant sensor data. Hence, the process in FIG. 19 can be applied to any hand-held based imaging system listed above.

In one embodiment, a Bayesian Approximate Extended Kalman Filter (AEKF) based inverse algorithm may be employed for image reconstruction (or tomogram generation) of 3-D optical property maps using location registered sensor data from the 3-D mesh of the target object. In brief, the AEKF-based algorithm may employ measurements and system errors to iteratively reconstruct for unknown parameters. The AEKF algorithm may be modified and/or optimized to reflect unique simultaneous illumination and detection measurement geometry of the imager described above, to apply noise filtration techniques to minimize artifacts during inversions; and/or to synchronize the mesh with the real-time co-registered measurements. These modifications may provide computationally efficient reconstructions. Various inverse algorithms have been developed by other researchers, and any one of them may be used instead of AEKF based algorithm.

The embodiments of the optical imaging system and method described above may use multiple simultaneous illuminating point sources with corresponding sequential/simultaneous multiple point detectors to maximize tissue volume illumination and reduce data acquisition times. The measurement geometry may be implemented as a sub-surface imaging geometry, which allows flexible imaging of large tissue volumes with minimal patient discomfort. The optical imaging system and method may have applications not only in breast imaging, but also for any other tissue or phantom imaging.

Moreover, the optical imaging system using tracking facilities and the location/sensor data registration process (FIG. 19) may provide a highly efficient method of reconstructing the optical property maps of 3-D tissue structures including 3-D sub-surface structures. Existing optical tomography towards breast cancer diagnostics is generally restricted to slab geometries representing compressed breast tissues or to cup-shaped breast phantoms of fixed volumes, wherein single point illumination configurations are typically employed. Compression of breast tissue is generally uncomfortable to patients and non-compressive techniques are usually preferred.

The invention claimed is:

1. A method of optically imaging a three-dimensional target object comprising:
generating a beam of light using a laser;
channeling the light beam into first ends of a plurality of optical source fibers;
manipulating the light beam to be simultaneously emitted through each of the plurality of optical source fibers;
disposing second ends of the optical source fibers on a plate;
conforming the plate along a surface of the target object;
illuminating the target object using the optical source fibers to perform simultaneous or sequential, multi-point illumination, from a plurality of angles;
disposing first ends of a plurality of optical detector fibers on the plate around the second ends of the optical source fibers;
receiving light from the target object into the plurality of optical detector fibers;
connecting second ends of the optical detector fibers to a detector; and
calculating a set of light characteristics based on signals received from the detector.

2. The method of claim 1, wherein the detector comprises a photo-detector array and a charge-coupled device.

3. The method of claim 1, wherein manipulating the light beam comprises collimating the light beam, diffusing the collimated light beam, and focusing the collimated and diffused light beam on a bundle of first ends of the plurality of optical source fibers.

4. The method of claim 1, further comprising calculating a value from a set of values including a frequency domain photon migration value, a continuous wave parameter value, or a time domain parameter value from the electrical signals based on the signals received from the detector.

5. The method of claim 1, further comprising disposing the light sources and detectors on a second plate, wherein the second plate is pivotable about the first plate.

6. The method of claim 1, further comprising scanning the target object to obtain a three-dimensional topographic map of the target object, tracing the plate on the target object, mapping the set of calculated light characteristics on the topographic map to generate a co-registered map of sensor and location data relevant for tomographic reconstruction.

7. A system including a hand-held probe and operable to provide optical imaging data of a three-dimensional target object, the system comprising:
a laser that generates light;
a first device for dividing the light into a plurality of beams;
a plurality of optical source fibers that channel the plurality of beams on to the target object;
a plurality of optical detector fibers that receive light from the target object;
a plate for terminating each of the plurality of optical source fibers and each of the plurality of optical detector fibers on a plane, the terminated source and detector fibers arranged to illuminate the target object from a plurality of angles and to receive light from the target object from a plurality of angles;

a charge-coupled device sensor that receives the light from the plurality of optical detector fibers and generates electrical signals corresponding;

a processor for computing a set of light characteristics based on the electrical signals.

8. The system of claim 7, wherein the first device comprises a bundle of first ends of each of the plurality of optical source fibers.

9. The system of claim 8, further comprising a collimator that receives the light from the laser and outputs a collimated light beam, a diffuser coupled between the collimator and the first device for evenly diffusing the light and a focuser for receiving the collimated and diffused light and channeling the collimated and diffused light over an area encompassing the bundle of first ends of the plurality of optical source fibers.

10. The system of claim 9, wherein the processor calculates a value from a set of values including a frequency domain photon migration value, a continuous wave parameter value, or a time domain parameter value based on the electrical signals.

11. The system of claim 7, wherein the plate is divided into a plurality of plate sections, wherein each plate section is pivotable about an edge with at least one other plate section.

12. The system of claim 7, wherein the plate comprises a flexible material adapted to conform to a surface of the three-dimensional object.

13. A hand-held optical imaging device for providing optical imaging data of a three-dimensional (3D) tissue comprising:

a support frame for positioning a plurality of plates on a surface of the tissue;

a plurality of optical source fibers having first ends arranged on the plurality of plates, such that the optical source fibers illuminate the tissue from a plurality of angles;

a plurality of optical detector fibers having first ends arranged on the plurality of plates around the first ends of the optical source fibers, such that the optical detector fibers receive light from a plurality of angles;

a light source for generating light;

a dividing device that receives the light from the light source and channels the light into second ends of the plurality of optical source fibers;

a detector coupled to second ends of the optical detector fibers; and a processing device for calculating a set of light characteristics from the tissue based on signals from the detector.

14. The device of claim 13, wherein the light source, the dividing device, and the plurality of optical source fibers are adapted to simultaneously emit light at each of the first ends of the optical source fibers at a substantially single level of intensity.

15. The device of claim 13, wherein the processor calculates a value from a set of values including a frequency domain photon migration value, a continuous wave parameter value, or a time domain parameter value based on the electrical signals.

16. The device of claim 13, wherein the plate comprises a plurality of plate sections and wherein the support frame couples a first plate section, a second plate section, and a third plate section, and further wherein the first and the third plate section are adapted to pivot about a first and a second edge, respectively, of the second plate section.

17. The device of claim 13, wherein the plate comprises a flexible material and wherein the support frame is adapted to conform the plate over a region of the tissue.

18. A method of providing sensor data of a three-dimensional (3D) tissue object comprising:

generating a three-dimensional topographic map of the tissue object using a surface rendering device;

tracing a probe on the surface of the tissue object to collect sensor data on a characteristic of the tissue object at a plurality of positions on the target object;

tracking the motion of the probe with respect to a reference point of the tissue object as the probe is traced on a surface of the tissue object;

mapping the sensor data of the tissue object on the three-dimensional topographic map with respect to the reference point, thereby generating location data for the sensor data; and processing the sensor data with location data to produce a co-registered map of sensor and location data relevant for reconstruction of a tomogram of the tissue object.

19. The method of claim 18, wherein the probe is an optical sub-surface imaging probe that provides sensor data for calculating a value from a set of values including a frequency domain photon migration value, a continuous wave parameter value, or a time domain parameter value based on the electrical signals.

20. The method of claim 18, wherein tracking the motion of the probe comprises disposing a first device of a pair of devices on the probe and a second device of the pair of devices at a fixed location with respect to the probe, wherein the pair of devices comprises a receiver and a transmitter.

21. The method of claim 18, wherein the transmitter device communicates with the receiver device using acoustic signals.

22. The method of claim 18, wherein the three-dimensional topographic map comprises a mesh of sub-surface point locations, and wherein processing the sensor data with location data to produce a co-registered map of sensor and location data relevant for reconstruction of a tomogram of the tissue object comprises producing the co-registered map sensor and location data based on the sub-surface point locations and sensor data.

* * * * *